United States Patent [19]

Grafe et al.

[11] Patent Number: 4,978,773

[45] Date of Patent: Dec. 18, 1990

[54] PROCESS FOR THE PREPARATION OF 2,6-DICHLORODIPHENYLAMINOACETIC ACID DERIVATIVES

[75] Inventors: Ingomar Grafe, Nuremberg; Helmut Schickaneder, Eckental; Kurt H. Ahrens, Nuremberg, all of Fed. Rep. of Germany

[73] Assignee: Heumann Pharma GmbH & Co., Nuremberg, Fed. Rep. of Germany

[21] Appl. No.: 369,618

[22] Filed: Jun. 21, 1989

[30] Foreign Application Priority Data

Jan. 27, 1989 [DE] Fed. Rep. of Germany ..... 89101437

[51] Int. Cl.$^5$ .......................................... C07C 227/18
[52] U.S. Cl. ..................................... 560/47; 562/456; 564/343; 564/202; 564/211; 548/486
[58] Field of Search ................. 560/47; 564/456, 343, 564/202, 211; 548/480

[56] References Cited

U.S. PATENT DOCUMENTS

| | | | |
|---|---|---|---|
| 4,242,522 | 12/1980 | Tsuchihashi et al. | 560/47 |
| 4,410,724 | 10/1983 | Takase et al. | 562/456 |

FOREIGN PATENT DOCUMENTS

| | | | |
|---|---|---|---|
| 2613838 | 10/1976 | Fed. Rep. of Germany | 562/456 |
| 59-20256 | 2/1984 | Japan | 562/456 |
| 1132318 | 3/1967 | United Kingdom | 560/47 |
| 2023578 | 1/1980 | United Kingdom | 562/456 |

OTHER PUBLICATIONS

Atkins et al., J. Med. Chem., vol. 26, p. 1361 (1983).
Kaltenbrann et al., Aryneim–Forsch, vol. 33, p. 62 (1982).

*Primary Examiner*—James H. Reamer
*Attorney, Agent, or Firm*—Burns, Doane, Swecker & Mathis

[57] ABSTRACT

A new process for the preparation of 2,6-dichlorodiphenylamine derivatives is described, which process provides the desired active compound in a high yield and with a very high degree of purity by a technically simple and realizable procedure.

4 Claims, No Drawings

PROCESS FOR THE PREPARATION OF 2,6-DICHLORODIPHENYLAMINOACETIC ACID DERIVATIVES 2,6-Dichloro-substituted diphenylaminoacetic acid derivatives play a major role in the therapy of rheumatic diseases, for which diclofenac sodium corresponding to formula I

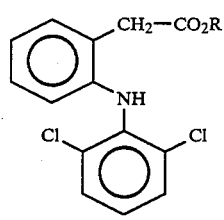

has proved to be particularly effective. This compound and its medical use has already been disclosed in DE-A-No. 15 43 639. The preparation of this compound generally proceeds via an intermediate product corresponding to formula V

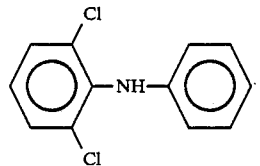

Various methods are already known for the preparation of this intermediate product which is the central structure of the above mentioned active compound. The disadvantages of these methods lie in the necessity of employing long reaction times and high temperatures and of providing only moderate to poor yields.

One known process for the preparation of the diphenylamine derivative corresponding to formula V proceeds from 2,6-dichloroacetanilide and bromobenzene and requires long reaction times, e.g. 96 hours (see D. C. Atkins et al., J.Med.Chem. 26, 1361 (1983); CH-PS No. 473 770 and U.S. Pat. No. 3,536,758). Another process uses iodobenzene as starting material but no yields are published for this process (see JP-OS-No. 57 167 947 and C.A. No. 98, 53 379 K (1983)).

In a more recent process (see J. S. Kaltenbronn, R. A. Scherer, Arzneim. Forsch. 33, 62 (1983)), the required substance is again only obtained in poor yields. In the process according to DE-OS No. 15 43 639, the yield obtained, as indicated there, is only 43% of the theoretical yield. According to the information given in the above mentioned documents, the intermediate product corresponding to formula V is obtained as a yellow oil. This substance, however, is a colourless solid (mp. 47.5°–48° C.).

JP-OS-No. 58 144 350 describes the Chapman rearrangement of N-phenyl-o-(2,6-dichlorophenyl)benzimidoester at 275° C. as an alternative for the preparation of compound V.

Direct processes for the preparation of diclofenac sodium have also been described, but they are not reproducible. In one known process of this type, 2-chlorophenyl acetic acid is reacted with 2,6-dichloroaniline (JP-OS-No. 81 158 744, C.A. 97, 23 467 z (1980)). The desired product, however, is only obtained in a yield of 37% after 12 hours in DMF at 150° C. Processes in which 2-bromophenyl acetic acid and 2,6-dichlorophenyl sodamide are used as starting materials also only provide low yields of the desired substance (22% in HMPT: see JP-OS-No. 77 00 240, C.A. 87, 39 078 c (1977)). Other processes employ molar quantities of iodine compounds (see JP-OS No. 80-66 550, C.A. 93, 167 946 v (1980) and DE-OS No. 29 32 198).

A process by which the desired compound corresponding to formula I is directly obtained from the compound corresponding to formula V is disclosed in CH-PS No. 473 770 and DE-OS-No. 15 43 639. This process is based on the known Stollé reaction (Ber. dtsch. Chem. Ges. 47, 2120 (1914) and is carried out in molten aluminium chloride.

It is an object of this invention to provide a technically simple process for the preparation of the compound corresponding to formula I by which the desired substance may be obtained in high yields and with a very high degree of purity from readily available starting materials without the extreme reaction conditions of the known processes required for the preparation of the sterically difficult molecule of formula V.

This problem is solved by the present invention. The invention relates to a process for the preparation of 2,6-dichlorodiphenylamine derivatives corresponding to the general formula I

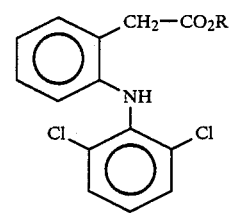

wherein R denotes a hydrogen atom, a $C_1$–$C_4$-alkyl group or an alkali metal atom, characterised in that a 2,6-dichlorophenoxyacetic derivative corresponding to formula II $$\text{(II)}$$

[structure: 2,6-dichlorophenyl–O–$CR_2R_3$–$CO_2R_1$]

wherein $R_1$ denotes a hydrogen atom or a $C_1$- to $C_6$-alkyl group and $R_2$ and $R_3$ each denotes a hydrogen atom or a $C_1$- to $C_4$-alkyl group is reacted with aniline in a one-shot reaction, first to form the compound corresponding to formula III $$\text{(III)}$$

[structure: 2,6-dichlorophenyl–O–$CR_2R_3$–CO–NH–phenyl]

wherein $R_2$ and $R_3$ have the meanings indicated above, which is then rearranged in situ to form the compound corresponding to formula IV

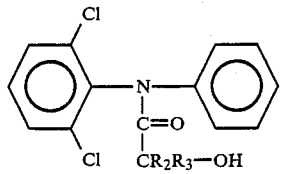 (IV)

wherein $R_2$ and $R_3$ have the meanings indicated above, and the resulting compound corresponding to formula IV is then aminolysed to form the compound corresponding to formula V

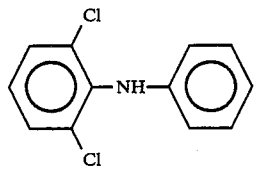 (V)

and after isolation of the compound corresponding to formula V, the latter is converted into the compound corresponding to formula VI

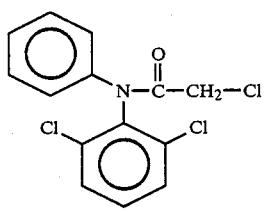 (VI)

by reaction with chloroacetyl chloride, and the compound of formula VI is cyclised to form the compound corresponding to formula VII

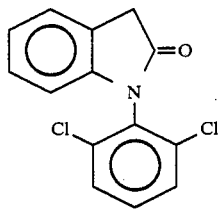 (VII)

and the resulting compound corresponding to formula VII is converted into the compound corresponding to formula I by alkaline hydrolysis.

In the first stage of the process according to the invention, a 2,6-dichlorophenoxyester corresponding to formula II

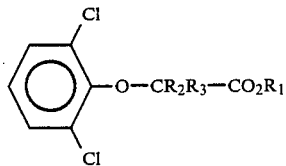 (II)

wherein $R_1$ denotes a hydrogen atom or a $C_1$- to $C_6$-alkyl group and $R_2$ and $R_3$ denote hydrogen or a $C_1$- to $C_4$-alkyl group is reacted with aniline in the presence of catalytic quantities of an alkali metal alcoholate such as sodium methanolate in an alcohol such as methanol, ethanol, n-propanol, i-propanol, n-butanol or i-butanol at temperatures below 120° C., for example at 90° C. preferably at 100° C.

According to a preferred embodiment of the invention, the starting compound corresponding to formula II is prepared from 3,5-dichlorohydroxybenzoic acid corresponding to formula VIII

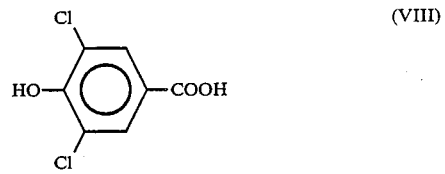 (VIII)

by first subjecting the compound corresponding to formula VIII in a one-shot reaction to a decarboxylation reaction in dimethylformamide or dimethylacetamide in the presence of catalytic quantities (e.g. 1/10 mol-%) of collidine at temperatures below 160° C., for example at 156° C., followed immediately by a reaction with a chloroacetic acid derivative corresponding to formula IX

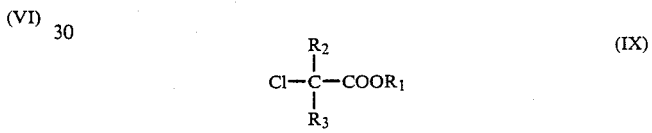 (IX)

Potassium carbonate may advantageously be used as base without the ester being saponified.

The intermediate compound corresponding to formula III may also be prepared directly from 2,6-dichlorophenol and chloroacetanilide by a base catalysed reaction but this procedure is not suitable for the preparation of large quantities of compound III on account of the toxic side effect of chloroacetanilide.

In the second stage of the process according to the invention, the intermediate compound of formula III obtained according to the invention is not isolated but directly rearranged in situ to the compound corresponding to formula IV

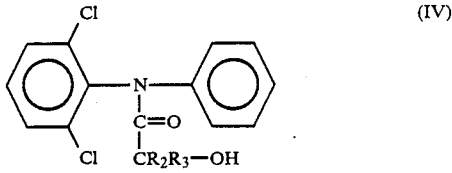 (IV)

at reaction temperatures of from 90° C. to 100° C., for example at 95° C. to 100° C. The rearrangement is brought about by the alkali metal alcoholate present in the reaction medium. As mentioned above, the reaction medium consists of an alcohol such as methanol, ethanol, n-propanol, i-propanol, n-butanol or i-butanol.

In the third stage of the process according to the invention, the compound of formula IV obtained by the molecular rearrangement is aminolysed to the compound corresponding to formula V

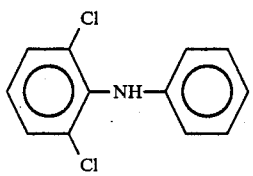

(V)

again without isolation, the aminolysis being brought about by the alkali metal alcoholate present in the reaction mixture. The reaction temperatures are the same as in the third stage of the process according to the invention. The 2,6-dichlorophenylamine of formula V obtained is isolated by the usual methods and optionally purified. The aforesaid compound is obtained in the form of a solid.

In the fourth stage of the process according to the invention, the compound corresponding to formula V is converted into the derivative corresponding to formula VI

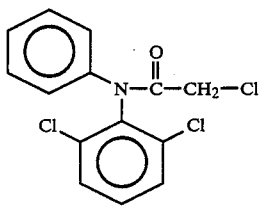

(VI)

by a reaction with chloroacetyl chloride. In the process according to the invention, chloroacetylation is preferably carried out as an aminolysis in an inert solvent, preferably xylene or chlorobenzene, at temperatures of from 90° C. to 120° C., preferably from 110° C. to 120° C. According to a preferred embodiment of the invention, this stage is carried out in the presence of catalytic quantities, e.g. from 1/20the mol-% to 1/10the mol-%, of 4-dimethylaminopyridine. The desired compound corresponding to formula VI is obtained in almost quantitative yields.

In the fifth stage of the process according to the invention, an intramolecular cyclisation of the compound of formula VI to the indolinone corresponding to formula VII

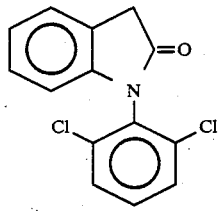

(VII)

takes place. This stage of the process according to the invention is carried out in an inert solvent, preferably o-dichlorobenzene, and at elevated temperatures, preferably at 140° C. to 160° C. Yields of over 90% are obtained.

In the last stage of the process according to the invention, the compound corresponding to formula VII is converted into the sodium salt of the desired compound of formula I by alkaline hydrolysis, preferably with sodium hydroxide solution in an alcohol as described above, in particular n-butanol. The reaction temperature at this stage is from 90° C. to 110° C., preferably from 100° C. to 110° C.

The resulting compound corresponding to formula I may be isolated from the reaction mixture by conventional methods, e.g. by extraction, and purified by conventional methods, e.g. by crystallisation.

It is to be regarded as an essential feature of the present invention that the first, second and third stage of the process are carried out as one-shot processes without isolation of the intermediate compounds III and IV. This not only simplifies the process but also provides relatively high overall yields, e.g. from 80% to 90% of the theoretical yield.

The invention will now be illustrated with the aid of the following Examples:

EXAMPLE 1

Preparation of 2,6-dichlorophenoxyacetic acid ethyl ester 675 g of 3,5-dichloro-4-hydroxybenzoic acid are introduced into 0.5 l of DMF at about 90° C. 75 ml of collidine are added and the reaction mixture is heated to 120° C. to bring about decarboxylation.

The sump temperature is slowly raised to 155° C. and this temperature is maintained until no more $CO_2$ evolves.

240 g of potash, 0.6 l of ethyl acetate and 0.35 l of ethylchloroacetate are added to the sump at 50° C. The reaction is left to proceed with liberation of $CO_2$ at 70° C. and the reaction mixture is then boiled under reflux for 2 hours. After the addition of 1.7 l of water, phase separation is carried out at 20° C. and the organic phase is fractionated.

Bp. 0.1=100 to 130° C.

Yield: 617 g=83% of th.

EXAMPLE 2

Preparation of 2,6-dichlorodiphenylamine

A mixture of 996 g of 2,6-dichlorophenoxyacetic acid ethyl ester, 500 ml of aniline and 400 ml of n-butanol is preheated to 100° C. in a distillation apparatus.

400 ml of 5.5N sodium methylate are run in over a period of 30 minutes during which a flow of distillate is maintained by the exothermic heat of the reaction. After addition of the sodium methylate, stirring is continued for 15 minutes at 100° C. with continued removal of distillate.

1 l of water is then added and solvent is distilled off down to the sump temperature of 90° C. Phase separation takes place at 60° C. The solvent is drawn off in a vacuum and the product is crystallised from 1 l of 90% i-propanol. The product is separated by suction filtration at 0° C. and washed with dilute i-propanol.

Yield: 727 g=76.5% of the theoretical yield with exploitation of the mother liquor to an extent of 82% of the theoretical.

$DSC_{max}$ =54° C. at a heating rate of 2 degrees Centigrade per min.

EXAMPLE 3

Preparation of N-(2,6-dichlorophenyl)indolinone(2)

476 g of 2,6-Dichlorodiphenylamine are introduced into 900 ml of o-dichlorobenzene and 271 g of chloroacetyl chloride are added at 150° C. in the course of 1.5 hours. Stirring of the mixture is continued for a further 2 hours at 150° C. until no more gases evolve.

533 g of aluminium chloride are added at 60° C. and the mixture is slowly heated to 160° C. Hydrogen chloride begins to evolve at 100° C. After one hour at 110° C, the reaction mixture is cooled to 60° C. and hydrolysed with 1.5 l of ice water at a maximum temperature of 80° C.

After phase separation, the reaction product is again washed with water and the solvent is drawn off under vacuum. The product is crystallised from 1 l of i-propanol.

Yield: 512 g=92% of theoretical yield.

$DSC_{max}$=121° C. at a heating rate of 2 degrees Centigrade per min.

EXAMPLE 4

Preparation of Diclofenac Sodium

1 Part of the indolinone from Example 3 is boiled in 2 parts of n-butanol and the equivalent quantity of sodium hydroxide solution with azeotropic removal of water, 0.2 parts of toluene being added.

When no more water separates and the salt has precipitated. 2 parts of i-propanol are added and the product is suction filtered at 10° C.

This product is recrystallised from water and dried at 100° C.

Yield: 88.6% of theoretical yield $DSC_{max}$=106° C. (of the hydrate).

$DSC_{min}$=268 to 270° C. at a heating rate of 2 degrees Centigrade per min.

We claim:

1. Process for the preparation of 2,6-dichlorodiphenylamine derivatives corresponding to the general formula I

[Structure of Formula I: phenyl ring with $CH_2-CO_2R$ group, NH linked to 2,6-dichlorophenyl] (I)

wherein R denotes a hydrogen atom, a $C_1$- to $C_4$-alkyl group or an alkali metal atom, characterised in that a 2,6-dichlorophenoxyacetic acid derivative corresponding to formula II

[Structure of Formula II: 2,6-dichlorophenyl-$O-CR_2R_3-CO_2R_1$] (II)

wherein $R_1$ denotes a hydrogen atom or a $C_1$ to $C_6$-alkyl group and $R_2$ and $R_3$ each denote a hydrogen atom or a $C_1$- to $C_4$-alkyl group is reacted with aniline in a one-shot process, first to form the compound corresponding to formula III

[Structure of Formula III: 2,6-dichlorophenyl-$O-CR_2R_3-CO-NH$-phenyl] (III)

wherein $R_2$ and $R_3$ have the meanings indicated above, and then to rearrange the compound of formula III in situ to form the compound corresponding to formula IV

[Structure of Formula IV: 2,6-dichlorophenyl-N(phenyl)-C(=O)-$CR_2R_3$-OH] (IV)

wherein $R_2$ and $R_3$ have the meanings indicated above, and the resulting compound corresponding to formula IV is aminolysed to the compound corresponding to formula V

[Structure of Formula V: 2,6-dichlorophenyl-NH-phenyl] (V)

and this compound corresponding to formula V is isolated and then converted into the compound corresponding to formula VI

[Structure of Formula VI: 2,6-dichlorophenyl-N(phenyl)-C(=O)-$CH_2$-Cl] (VI)

by a reaction with chloroacetyl chloride, and the compound corresponding to formula VI is cyclised to the compound corresponding to formula VII

[Structure of Formula VII: indolinone fused system with N-(2,6-dichlorophenyl), C=O] (VII)

and the resulting compound of formula VII is converted into the compound corresponding to formula I by alkaline hydrolysis.

2. Process according to claim 1, characterised in that the compound corresponding to formula II is prepared by a one-shot reaction from 3,5-dichloro-4-hydroxybenzoic acid corresponding to formula VIII

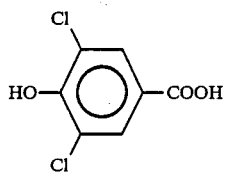
(VIII)

by decarboxylation in dimethylformamide or dimethylacetamide in the presence of catalytic quantities of collidine and reaction with a chloroacetic acid derivative corresponding to formula IX

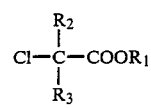
(IX)

wherein $R_1$, $R_2$ and $R_3$ have the meanings defined in claim 1.

3. Process according to claim 1, characterised in that the preparation of the compound corresponding to formula V is carried out in an alcohol at temperatures below 120° C. in the presence of catalytic to equimolar quantities of an alkali metal alcoholate.

4. Process according to claim 1, characterised in that the reaction of the compound corresponding to formula V with chloroacetyl chloride is carried out as an aminolysis and the resulting compound corresponding to formula VI is cyclised to the compound corresponding to formula VII in o-dichlorobenzene and this compound of formula VII is converted into the compound corresponding to formula I by means of an alkali liquor in a protic solvent.

* * * * *